US00RE39789E

(19) United States
(12) Reissued Patent
Raulet et al.

(10) Patent Number: US RE39,789 E
(45) Date of Reissued Patent: Aug. 21, 2007

(54) TUMOR THERAPY

(76) Inventors: David H. Raulet, 485 Life Sciences Addition, UCB, Berkeley, CA (US) 94720-3200; Andreas Diefenbach, 485 Life Sciences Addition, UCB, Berkeley, CA (US) 94720-3200

(21) Appl. No.: 11/057,105

(22) Filed: Feb. 11, 2005

Related U.S. Patent Documents

Reissue of:
(64) Patent No.: 6,821,522
Issued: Nov. 23, 2004
Appl. No.: 09/871,491
Filed: May 31, 2001

(51) Int. Cl.

| | |
|---|---|
| ***A61K 39/00*** | (2006.01) |
| ***A61K 39/38*** | (2006.01) |
| ***A61K 48/00*** | (2006.01) |
| ***A01N 63/00*** | (2006.01) |
| ***A01N 65/00*** | (2006.01) |

(52) U.S. Cl. ..... 424/277.1; 424/93.1; 424/93.2; 424/184.1; 424/145.1; 435/4; 435/71; 435/7.21; 435/7.23; 435/7.92; 435/325; 436/64; 436/86; 436/87; 436/164; 514/1; 514/2; 514/4; 514/8; 514/12; 514/23; 514/53; 514/54; 530/350; 530/385; 530/386; 530/387.1; 530/388.1; 530/389.1

(58) Field of Classification Search ..... 424/93.1, 424/93.2, 184.1, 277.1, 145.1; 435/4, 7.1, 435/7.21, 7.23, 7.92, 325; 436/64, 86, 87, 436/164; 514/1, 2, 4, 8, 54, 12, 23, 53; 530/350, 530/385, 386, 387.1, 388.1, 389.1
See application file for complete search history.

(56) References Cited

U.S. PATENT DOCUMENTS

2004/0115198 A1 * 6/2004 Spies et al. ..... 424/145.1

FOREIGN PATENT DOCUMENTS

| | | | |
|---|---|---|---|
| WO | WO98/19167 A | | 5/1998 |
| WO | WO 98/19167 | * | 5/1998 |
| WO | WO99/31241 A | | 6/1999 |
| WO | WO01/71005 A | | 9/2001 |

OTHER PUBLICATIONS

Diefenbach et al. Ligands for the murine NKG2D receptor: expression by tumor cells and activation of NK cells and macrophages. Nature Immunology 1(2): 119–126, Aug. 2000.*

Gura. Cancer Models: Systems for Identifying New Drugs Are Often Faulty. Science 278:1041–1042, 1997.*

Diefenbach et al., Natural Killer Cells: Stress Out, Turn On, Tune In, Current Biology, Current Science, 9 (22), R851–R853 Nov. 18, 1999.

Pende et al., Role of NKG2D in Tumor Cell Lysis Mediated by Human NK Cells . . . , Nonepithelial Origin, Eur J Immunol 31 (4), 1076–1086 Apr. 2001.

Bauer et al., Activation of NK cells and T cells by NKG2D . . . , Science 285 (5428), 727–729, Jul. 30, 1999.

Diefenbach et al., Rae1 and H60 Ligands of the NKG2D receptor stimulate tumor immunity, Nature 413, 165–171, Sep. 13, 2001.

Diefenbach et al., Strategies for target cell recognition by natural killer cells, Immunol Reviews 181, 170–184, Jun. 2001.

* cited by examiner

*Primary Examiner*—Alana M. Harris

(57) ABSTRACT

Neoplasia is treated by administering to a mammalian host a composition comprising ligands for the NKG2D receptor. In addition, other NKG2D ligands, proteins specific for the neoplastic cells and cytokines may be included to enhance the immune response. The composition may be cells comprising expression constructs for the ligands, liposomes or combinations of protein molecules.

21 Claims, No Drawings

TUMOR THERAPY

Matter enclosed in heavy brackets [ ] appears in the original patent but forms no part of this reissue specification; matter printed in italics indicates the additions made by reissue.

The invention described herein was supported in part by a grant (*NIH Grant No. A135021*) from the National Institute of Health. The U.S. government may have rights in this application and any patent issuing thereon.

INTRODUCTION

1. Field of the Invention

The field of this invention is treatment of neoplasia.

2. Background of the Invention

Natural killer cells attack many tumor cell lines in vitro, and, after activation, can attack primary tumor cells[1]. NK cells have therefore long been thought to be involved in tumor surveillance and to be an important part of anti-tumor immunity[2-8], but the basis for the interaction between NK cells and tumor targets remains largely unknown. Recently, the stimulatory lectin-like NKG2D receptor has been characterized[9-15]. In mice, the receptor is expressed by NK cells, activated CD8+ T cells and activated macrophages, and receptor engagement can stimulate or costimulate these cells[14-15]. Several distinct families of cell surface ligands for NKG2D have been identified, all of which are distantly related to class I MHC molecules[13-16]. These ligands are often expressed at high levels by tumor cells, but not by normal cells in mature animals[14,15,17,18]. While the prevalence of these ligands on highly tumorigenic cells suggests they might provide a target for therapeutic intervention, it also suggested that their presence is insufficient to provoke a host rejection of the tumor.

We disclose here the remarkable development of methods whereby, contrary to expectations, NKG2D ligands can indeed be exploited to provoke a host response to inhibit tumor growth. Our methods are also effective prophylactically, to inhibit tumor formation, and remarkably, are effective against both tumors expressing the ligands and tumors which do not.

Relevant Literature

Diefenbach, et al., Nature Immunology 1, 119–26 (2000) describe ligands for the mNKG2D receptor and activation of NK cells and macrophages in mice. Relevant information was disclosed at the Keystone Conference, Jan. 1, 2001 and Gordon Conference, Feb. 1, 2001. Smyth, et al., Nature Immunology 2, 293–9 (2001) discuss therapeutic immunity to cancer. Li, et al., Nature Immunology 2, 443–51 (2001) report MICA as a stress inducible ligand for NKG2D and the crystal structure of the complex. A CTLA-4 blockade to enhance immune response is reported in U.S. Pat. No. 6,051,227.

SUMMARY OF THE INVENTION

The invention provides methods for inhibiting tumor growth. The methods may be therapeutically applied to a mammalian host expressing native NKG2D and determined to harbor a tumor arising in situ and comprising tumor cells, and/or prophylactically applied to a mammalian host expressing native NKG2D and determined to be predisposed to harboring a tumor arising in situ.

The general methods involve administering to the mammalian host a composition comprising a multivalent NKG2D-binding agent, wherein the administering step is effective to inhibit growth of the tumor; and detecting a resultant inhibition of growth of the tumor.

In particular embodiments, the tumor cells provide one or more of the following characteristics: are melanoma cells; present downregulated MHC class I proteins; express a native NKG2D ligand; express a substantially undetectable amount of NKG2D ligand; are substantially non-immunogenic; are highly metastatic; and are highly tumorigenic.

In a particular embodiment, the administering is remote from the tumor.

In particular embodiments, the agent comprises: a multivalent NKG2D-specific antibody; a multivalent NKG2D ligand comprising a plurality of covalently linked natural NKG2D ligand moieties; a multivalent NKG2D ligand comprising a plurality of non-covalently linked natural NKG2D ligand moieties, wherein the moieties are restricted to a common presenting surface, particularly wherein the common presenting surface may be of a host-compatible (such as host- or tumor-derived) cell transformed to express the ligand moieties; and/or a multivalent NKG2D ligand comprising a plurality of natural NKG2D ligand moieties, such as MICA, MICB and ULBP ligand moieties.

Accordingly, cancer treatment is provided by administering binding agents, such as ligands for the NKG2D receptor in vivo to activate immune cells present in a host to enhance the immune response to cancer cells. The ligands are presented by themselves or in conjunction with other compounds that may serve as immune system activators and/or provide for greater specificity for the target. The ligands are administered in a form that results in the aggregation or multimerization of the receptor, such as multivalent form, such as bound to membranes, linked together, or expressed on genetically modified cells.

DETAILED DESCRIPTION OF THE INVENTION

The following descriptions of particular embodiments and examples are offered by way of illustration and not by way of limitation. Unless contraindicated or noted otherwise, in these descriptions and throughout this specification, the terms "a" and "an" means one or more, the term "or" means and/or.

The present invention provides methods for dramatically enhancing the immune response to cancer cells by administering multivalent NKG2D ligands, particularly in the form of cells or cell mimics that express or overexpress on their surface NKG2D ligands. For example, patients with a preexisting tumor are treated with cells or cell mimics expressing NKG2D ligands, and optionally tumor antigens, to enhance the immune response against the tumor and promote regression or rejection of the tumor and/or any metastases. Typically, the patient's tumor is biopsied and the tumor cells are transduced or transfected with NKG2D ligands to effect an increased level of cell surface expression. The engineered cells are reinfused to provoke or enhance an anti-tumor immune response. Alternatively, cell mimics may be used, such as beads or vesicles coated with NKG2D ligands, peptide-loaded MHC molecules, and optionally other stimulatory molecules, such as adhesion molecules (e.g. ICAM-1) or costimulatory molecules (e.g. B7.1 or B7.2). The subject methods are advantageously combined with other therapies for enhanced, synergistic effect. For example, in one such embodiment, the tumor cells are engineered to coproduce a cytokine such as GM-CSF or employed in conjunction with CTLA-4 blockade therapy.

Similar methods employ multivalent NKG2D ligands and tumor antigens as a host vaccine against predisposed primary tumors and metastases. For example, patients without confirmed tumors are treated with cells or cell mimics presenting NKG2D ligands to provoke protective immunity to tumor formation or progression. The cells or mimics may optionally present one or more tumor antigens, optionally in conjunction with MHC molecules that present peptides corresponding to tumor antigens, preferably loaded with the tumor antigen peptide.

The invention provides methods for inhibiting tumor growth. The methods may be therapeutically applied to a mammalian host expressing native NKG2D and determined to harbor a tumor arising in situ and comprising tumor cells, and/or prophylactically applied to a mammalian host expressing native NKG2D and determined to be predisposed to harboring a tumor arising in situ and comprising tumor cells.

The general methods involve administering to the mammalian host a composition comprising a multivalent NKG2D-binding agent, wherein the administering step is effective to inhibit growth of the tumor; and detecting a resultant inhibition of growth of the tumor. In therapeutic applications, the host is determined to harbor a tumor arising in situ; whereas in prophylactic applications, the host is determined to be predisposed to harboring a tumor arising in situ. The tumor may have arisen from a known or predetermined initiator, such as a retrovirus, carcinogen or irradiation. More typical in the case of preferred human hosts, the tumor is naturally occurring and spontaneous. The methods are shown to be effective against a wide variety of tumor types, including solid or hematological tumors, exemplified by melanoma, lymphomas, plasmacytoma, sarcomas, glioma, thymoma, leukemias, breast cancer, prostate cancer, colon cancer, esophageal cancer, brain cancer, lung cancer, ovary cancer, cervical cancer, hepatoma, astrocytoma, neuroblastoma, meningioma, etc.

The tumor cells may express a native NKG2D ligand or may express a substantially undetectable amount, particularly no detectable amount of a native NKG2D ligand. Preferred target tumor cells are substantially non-immunogenic, meaning substantially less immunogenic relative to most same tissue type tumors. Preferred target tumor cells are often relatively highly metastatic and relatively highly tumorigenic and frequently present downregulated MHC class I proteins.

A wide variety of multivalent NKG2D-binding agents may be used, so long as the agent effects immune cell activation against the tumor cells and a resultant inhibition of tumor growth. In one embodiment, the agent comprises a multivalent somatically recombined NKG2D-specific receptor like NKG2D-specific antibodies or T-cell antigen receptors; methods for making specific immune receptors, such as polyclonal and monoclonal antibodies, are well known in the art; see, e.g. Harlow and Lane (1988) Antibodies, A Laboratory Manual, Cold Spring Harbor Laboratory.

In another embodiment, the agent comprises a multivalent NKG2D ligand comprising a plurality of linked NKG2D binding moieties. The NKG2D binding moieties may be natural NKG2D ligands (e.g. H-60, Rae1 proteins, ULBP and MIC proteins, such as Rae1 α, Rae1 β and Rae1 γ, particularly natural human MICA, MICB, ULBP1, ULBP2 and ULBP3 proteins), fragments, agonists, or antagonists thereof, so long as the requisite NKG2D binding is effected. The binding moieties may be linked covalently or noncovalently, directly or through a linker molecule, by any of a variety of well-known and convenient protocols, e.g., Uy R, Wold F. Adv Exp Med Biol, 86A:169–86, 1977; Brunner, Annu Rev Biochem 62:483–514, 1993. Crosslinking agents include formaldehyde, malondialdehye, succindialdehyde, activated malonic acid, activated succinic acid, etc.

In a particular embodiment, the binding moieties are linked by being restricted to a common presenting surface. A wide variety of presenting surfaces and modes of attachment thereto may be employed. For example, a plurality of binding moieties may be covalently coupled to a microbead, noncovalently incorporated into liposomes, microsomes or cell ghosts or other membraneous cell mimics, etc. In a preferred embodiment, the binding moieties are restricted to a host-compatible cell (i.e. immunologically compatible cell), particularly a host or tumor-derived cell, transformed to express the binding moieties. The compositions may be combined with compounds that enhance the response, such as cytokines, adjuvants, antigens, etc., particularly antigens associated with the target tumor cells.

Where practiced with genetically modified cells, the genetic modification can be performed in vivo or in vitro. Bare DNA having an expression construct for the ligand(s) or viruses, e.g. retroviruses, can be introduced into cells under conditions whereby the ligand(s) is expressed. The cells may be tumor cells present in the host, tumor cells isolated from the host, allogeneic cells, particularly of the same type as the tumor cells, allogeneic cells expressing at least one of class I MHC or class II MHC determinants, wherein at least one class I MHC or class II MHC determinant is syngeneic to a recipient and wherein at least one class I MHC or class II MHC determinant is allogeneic to the recipient, and expressing at least one antigen in the T cell repertoire, particularly associated with the target tumor cell, more particularly an antigen unexpressed in the normal cell and expressed in the tumor cell (See, U.S. Pat. No. 6,187,307). Autologous cells may be used and transduced or transfected with genes that express at least an active portion of at least one of the ligands in conjunction with at least one gene that is specific for the tumor cell, as well as other protocols that can be used to advantage.

The cells may be transduced with DNA, using various techniques, such as calcium precipitation. See, for example, Montigny, et al., Nucleic Acids Res. 29:1982–8, 2001; Purpus and McCune, Int. J. Dev. Biol. 37:117–24, 1993. Alternatively, a wide variety of viruses may be used for transfection in vivo and in vitro. Viruses that have found use include retroviruses, adenovirus and adeno-associated virus, lentiviruses, and herpes simplex virus, among others. See, for example, Bradley, et al., J. Immunol, 159:1086–95, 1997; Zhing, et al., J. Biol. Chem. 2001, Apr. 19 issue; Eckert, et al, Bone Marrow Transplant Suppl 2:3114–7, 2000; Rea, et al., J. Immunol. 166:5236–44, 2001; Braun-Falco and Halleck, Arch. Dermatol. Res. 293:12–7, 2001; Luther-Wyrsik, et al., Hum. Gene Ther. 12:377–89, 2001; Salmon, et al., Blood 96:3392–8, 2000; Kircheis, et al., Cancer Gene Ther. 7:870–8, 2000; Huddle, et al. Cornea 19:369–73, 2000. Alternatively, microinjection may be employed. Davis, et al., Curr. Opin. Mol. Ther. 2:412–9, 2000. Other techniques include lipofectin-mediated and electroporation-mediated fusion. The particular manner in which the nucleic acid is introduced into the cells will vary with the nature of the cells, the nature of the construct, the efficiency of introduction of the genes and the efficiency of expression, the size of the DNA being introduced, the vector used for introducing the DNA, etc.

One or more genes may be introduced concurrently or consecutively, usually at the same time, where one or two different constructs may be introduced into the cell. In addition to the NKG2D ligand(s) genes, other genes may also be introduced to enhance the activation of the target cells or to select particular types of cells. Various proteins can be employed that are associated with one or more cancer cell types. For example, Her-2 and MUC-B1 are associated with breast cancer, Cooke, et al., Eur. J. Cancer 2001, 37 Suppl 1:3–10 and WO98/48014; Ki-67, and adenoma antigen is associated with anogenital lesions and colorectal cancer, Caloree, et al., Dis. Colon Recturm 2001, 44:523–33 and 534–7; M2-PK, CYFRA 21.1, NSE, LCGA epitopes mucin and HCAVIII are associated with lung cancer and in some gastrointestinal cancers, Schneider, et al., Anticancer Res. 2000, 20(6D):503–8, WO00/75190, WO98/12564 and WO96/02552; and other generic markers, such as the oncogenes, myc, ras, and erbB, ATM variants, etc. Other tumor associated antigens reported in U.S. Pat. No. 6,187,307 include genes of the MAGE family, BAGE, tyrosinases, CEA, CO17-1A, MART-1, gp100, TAG-72, MUC-1, CA 125, decapeptide 810, P1A, mutated p53, and tumor associated viral antigens. (Shawler, et al., Advances in Pharmacology 1997, 40:309–337). Genes expressing the entire protein or fragments thereof comprising an immunodominant sequence may be employed. Desirably, a fragment of the gene will be presented by the host class I MHC, so as to enhance the recognition by the $CD8^+$ T cells of the tumor cells present in the host.

In addition or alternatively to the cancer related genes, other genes may be introduced that will enhance the cellular response by serving to activate the target lymphocytes, enhance proliferation, enhance protective mechanisms, and the like. Expression products of interest include Il-4, IL-12, TNF-α, IFN-γ, GM-CSF, G-CSF, etc., where other cytokines may find use, such as other interleukins, interferons, and the like.

Liposomes may be used for delivery of proteins and genes, where the components may be in the lumen or bound to the membrane, where the liposomes may be unilamellar or multilamellar. Description of preparing liposomes may be found in Nakano, et al., Bioconjug. Chem. 2001, 12:391–5; Ignatius, et al., Blood 2000, 3505–13. Using tumor associated antigens and liposomes is described by Bergers, et al., Cancer Immunol. Immunotherap. 1993, 37:271–9; Kwak, et al., J. Immunol. 1998, 160:3637–41; Bakouche and Gerlier, Immunology 1986, 58:6507–13; Bragman, et al., Biochim. Biophys. Acta 1983, 130:187–95. The composition of the liposomes may be selected to provide enhanced stability, enhanced immune response, ease of preparation and the like. The liposomes may be prepared in situ or ghosts may be employed. See, for example, Krishman, et al., J. Immunol. 2000, 165:5175–85.

When it is desired that the proteins be expressed in cells, expression constructs are prepared for introduction into the cells. The manner in which constructs are prepared is well established in the literature. See, for example, Sambrook and Russell, Molecular Cloning: A Laboratory Manual 3$^{rd}$ ed., Cold Spring Harbor Laboratory Press, NY. Expression can be achieved by employing transcriptional regulation elements that control the transcription of the gene and are active in the target cell. The regulatory region comprises a promoter, which may be constitutive or inducible, may comprise an enhancer that is responsive to transcription factors produced by the target cell, and will include other members involved with transcriptional or translational regulation, such as the TATA box, CAAT box, suppressors, combinations of promoters, etc. The various components of the regulatory region are commercially available or may be isolated from known sequences and linked together or synthesized in accordance with known ways, where adapters may be employed for linkage. By employing vectors where sequences can be inserted at appropriate sites to build the expression construct, long expression constructs of one or more genes may be constructed. Besides the genes of interest, one may have gene markers that allow for selection of cells in which the construct has stably integrated, such as antibiotics, fluorescent proteins, and/or genes that complement an auxotroph. These genes are well known and include G418 (neo), chloramphenical resistance, tetracycline resistance, green fluorescent protein, etc.

The transcriptional regulatory region may be selected to preferentially be transcribed in specific cell types, producing the necessary transcription factors. The regulatory region may be one that regulates the transcription of a protein in particular cells, normal or tumorous. See, for example, Horimoto, et al., Cancer Gene Ther. 2000, 7:1341–7; Ludewig, et al., Vaccine 200019:23–32; Yamagawa, et al., J. Gastroenterol. Hepatol. 2000, 15:5412–9. This approach is particularly useful with a virus as a vector for introduction of genes. Replacing the viral promoter for an essential viral gene with a transcriptional regulatory region that is specific for the target cells allows for administration of the virus at a site other than the tumor and restriction of viral proliferation in the tumorous cells or the same type of cells as the tumor. (By "specific" is not intended that it be unique, only that it is not universally functional in all cells, preferably it is functional only in a few types of cells and more preferably, it is substantially unique to the neoplastic target cells. The term "specific" is used in the same manner when associated with other constructs.) The fewer cells in which the transcriptional regulatory region is functional, the more specific will be the treatment. It also allows for treatment of metastatic cancer, since the virus will invade and proliferate in all of the same type of cells, regardless of location.

Instead of natural ligand or active fragments thereof, one may use mimics. By mimic is intended any compound that can compete with the ligand for binding to the NKG2D receptor, particularly one that prevents at least 50% binding of the ligand in the presence of the compound at comparable concentrations. There are numerous methods for preparing and screening compounds. A variety of procedures have been developed for preparing large libraries, referred to as combinatorial libraries, and screening for compounds having an affinity for a target compound. See, for example, U.S. Pat. Nos. 6,207,861; 6,001,579; 5,741,713; 5,565,324 and PCT published applications WO00/113126; WO00/79268; WO98/41869; WO93/13423. The screening can be performed in a variety of ways where the ligand competes with the candidate compound. For example, the receptor can be labeled with a detectable label, e.g. a fluorescer, the ligand can be bound to a solid surface, e.g. a magnetic particle, well wall, etc. and the candidate compound combined with the ligand and receptor under binding conditions. The amount of receptor that binds to the ligand will be directly related to the amount of candidate compound that binds to the receptor, so that measuring the fluorescence bound to the surface or in solution will determine the affinity of the candidate compound for the receptor. Alternatively, one may use cells expressing the NKG2D receptor on their surface, allow the candidate compound and ligand to compete for the receptor and then separate the cells from the supernatant. By adding fluorescent antibody for the ligand to the cell precipitate, dispersing and washing and then precipitating the cells, the fluorescence of the cellular composition will be related to the affinity of the candidate compound. Numerous other assay techniques are available for screening candidate-binding compounds that will directly compete with the ligands of interest.

Where one wishes to determine whether the candidate compound will activate the target NK cell, one uses NK cells to which the candidate compound is added in one vessel and to which a ligand is added in another vessel. One then assays for a product produced as a result of the activation, such as a cytokine, and compares the results from the candidate compound and the ligand. The methodology used in the Experimental section demonstrates methodology for evaluating activation of NK cells. Compounds that show high binding affinity may then be used in place of the ligand in competitive assays and for the development of drugs. By observing the changes in activity of compounds based on structure, the structure-activity relationship may be analyzed using a data processor to provide candidate structures for drugs.

The manner of administration of the product used for the treatment may be applied in various ways depending on the nature of the administered agent. The administration may be by any convenient means, such as injection, ingestion, inhalation, transfusion, implantation or transplantation. Cells or liposomes containing the NKG2D ligands may be advantageously administered by injection at various sites, such as intratumorally, subcutaneously, intraperitoneally, intramuscularly, intraarterially, intravenously, etc. The particular site will depend to some degree on the nature of the tumor, the response of the host to a particular site, and the nature of the product being administered. In a particular embodiment, the administering is remote from the tumor. The number of cells or liposomes administered will usually be at least about $10^3$, more usually at least about $10^4$, and not more than about $10^{10}$, usually not more than about $10^8$. A single administration may be used or a plurality of administrations, where one or more injections may be used for a single administration, usually at the same site. Generally, if a course of treatment is used, the administrations will occur at two to four week intervals.

The cells will be formulated in an appropriate medium for administration. Various buffers may be employed, such as phosphate buffered saline, RPMI, saline, aqueous alcohol, lipids, etc., where the volume may vary from about 100 μl to 2 ml, usually from about 0.5 ml to 2 ml in humans and proportionately in other mammals. Various adjuvants and/or emulsifiers may be used to enhance the response, such as LPS, alum, incomplete Freund's adjuvant (IFA), liposyn, saponin, squalene, L121, emulsigen, monophosphoryl lipid A (MPL), QS21, and ISA 720, ISA 51, ISA 35 or ISA 206 as well as other efficacious adjuvants and emulsifiers.

Where nucleic acid is administered, it will be administered in a manner consistent with the nucleic acid being administered. For bare DNA, the nucleic acid will normally be injected into the tumor under conditions where the DNA will be taken up by the cells and expressed. For viruses, administration will depend upon whether the virus is capable of proliferation, is constructed to be limited to particular cell types, and/or has previously caused an immune response in the host, the nature of the virus and its cell specificity, and the like. The particular manner of administration will be selected to enhance the effectiveness of the transformation or transfection of the host cells.

The subject treatment may be used in conjunction with other treatments, such as chemotherapy, radiation, etc.

Once the host has been treated, the host may be monitored for the effect on the tumor. Various markers are shed, so that the blood level of such markers may be determined, e.g. PSA, CEA, etc. Using PET, one may observe the size of the tumor and in some instances, the size of the tumor may be defined by palpation, observation, etc. Depending on the response of the host, one or more repetitive administrations of the subject composition may be performed.

Depending on the nature of the compositions of the subject invention, the compositions may be provided as kits. For example, the nucleic acids and liposomes can be provided in an appropriate formulation with immune adjuvants in the same or different containers, with sterile buffer, syringes or catheters, and the like.

The following examples are offered by way of illustration and not by way of limitation.

EXAMPLES

I. Ligands of the NKG2D receptor stimulate rejection of tumor cells and induce protective immunity to tumor cells.

Here we demonstrate that ectopic expression of the murine NKG2D ligands Rae1 β or H60 in several tumor cell lines results in dramatic rejection of the tumor cells by syngeneic mice. Strikingly, mice that reject tumor cell lines expressing Rae1 or H60 are immune to subsequent challenge with tumor cells lacking NKG2D ligands, supporting application of the ligands in the design of tumor vaccines.

As demonstrated by staining with a tetramerized derivative of the extracellular portion of NKG2D, NKG2D ligands are expressed by the majority of tumor cells tested, including various lymphoid, myeloid, and carcinoma cell lines[14], Northern blot analysis revealed that many of the positive cell lines express Rae1 transcripts, while H60 transcripts were limited to only one or two, indicating that these genes are specifically upregulated in tumor cell lines.

To determine whether tumor cells expressing NKG2D ligands stimulate anti-tumor immune responses, we used a retrovirus expression system to ectopically express high levels of Rae1 β or H60 in EL4, a thymoma, RMA, a T cell lymphoma and B16-BL6, a melanoma. These cell lines are all from C57BL/6 (hereafter B6) mice and do not normally express NKG2D ligands[14]. Murine B16 melanoma cells are frequently employed for in vitro and in vivo antitumor studies, as they originated from a spontaneous tumor and thus have low immunogenicity, similar to most human tumors. Ligand-expressing cells were selected based on staining with NKG2D tetramers. To serve as controls, tumor cells transduced with empty retrovirus vector (designated as EL4/-, B16/- and RMA/-) were selected by genomic PCR (see Methods).

For analysis of the response to EL4 and B16-BL6 tumor cells, groups of five B6 mice were inoculated subcutaneously with syngeneic tumor cell transductants. Control-transduced EL4 or B16-BL6 cells grew progressively at a rate similar to untransduced cells, leading to uniform terminal morbidity by approximately 28 days. Strikingly, Rae1 β- or H60-transduced tumor cells of both types were rejected rapidly and completely, as they failed to yield detectable tumors at any time point. With a higher dose ($1\times10^5$) of Rae1 β- or H60-transduced B16-BL6 cells, tumors grew progressively in all the mice, but growth was delayed by more than two weeks compared to the control-transduced tumor cells. Ligand transduced tumor cells of both types also failed to grow in B6 mice that had been depleted of CD8+ T cells or in B6-Rag1$^{-/-}$ mice, which lack all T and B cells, but grew progressively in normal and B6-Rag1$^{-/-}$ hosts that had been depleted of NK1.1$^+$ cells. Thus, these doses of Rae1 β- or H60-transduced EL4 cells and B16-BL6 cells are rejected rapidly by conventional NK cells without a requirement for T and B cells.

Rae1 β- or H60- expression by B16-BL6 cells also reduced the frequency of lung metastases by over 10-fold after i.v. injection. In another experiment where mice were examined at a later time point, control-transduced B16-BL6 cells formed massive contiguous lung metastases, but ligand-transduced B16-BL6 cells were almost completely rejected. NK1.1-depletion before tumor cell inoculation dramatically depressed the rejection of the tumor cells.

Rae1 β- or H60-transduced RMA tumor cells were also rejected by B6 mice. Unlike the responses to the other tumor cells, however, the rejection of ligand-transduced RMA cells was mediated by both CD8+ T cells and NK cells, though the specific outcome depended on the dose of tumor cells. Depletion of both NK1.1$^{+}$ cells and CD8+ T cells was necessary to abrogate rejection of the smallest inoculum of 104 ligand-transduced tumor cells, while depletion of either population allowed tumor growth in at least some animals injected with the largest dose of $10^6$ tumor cells. With the intermediate dose of $10^5$ tumor cells, depletion of CD8 cells allowed tumor cell growth, but NK cell depletion did not. Thus, either subset is sufficient for tumor rejection at the lowest tumor cell dose, CD8 cells (but not NK cells) are sufficient at the intermediate dose, and the two cell types must cooperate to achieve consistent rejection at the highest tumor cell dose. In B6-Rag1$^{-/-}$ mice, NK cells were sufficient to reject the Rae-1b- or H60-transduced RMA cells at the two lower tumor doses, indicating that NK cells are more active or effective in these B6-Rag1$^{-/-}$ mice than in B6 mice. Parallel analysis of mice inoculated with the RMA/S cell line, an MHC class I$^{low}$ version of RMA cells, confirmed previous reports that these cells are rejected by NK cells and not CD8+ T cells[2], and demonstrated the efficacy of our NK cell depletion procedure.

When inoculated intraperitoneally, RMA/S cells, but not RMA cells, locally recruit NK cells and enhance their sensitivity to subsequent stimulation[19]. Similarly, i.p. inoculation of Rae1 β- or H60-transduced RMA tumor cells increased the number of peritoneal NK cells 2–4-fold, and enhanced the cytotoxic activity of the cells versus YAC-1 target cells or Rae1 β-transduced RMA target cells, but not against RMA cells. The cytotoxic activity was nearly eliminated when NK1.1$^{+}$ cells were depleted prior to the assay. A substantially higher fraction of these NK cells also produced IFN-g after in vitro stimulation with YAC-1 tumor cells, but not with RMA cells. Similar results were obtained with ligand-expressing B16-BL6 and EL4 cells. Thus, expression of NKG2D ligands, like MHC-deficiency, provokes NK cell recruitment and sensitization in vivo.

To address whether prior immunization with tumor cells expressing NKG2D ligands induces protective immunity to ligand-negative tumor cells, mice that had previously rejected Rae1 β- or H60-transduced tumor cells (EL4, B16-BL6 or RMA cells) were rechallenged with corresponding ligand-negative tumor cells 8–12 weeks after the first exposure. The ligand-negative tumor cells grew progressively in naïve B6 mice, but were rejected by the mice that had been previously exposed to the corresponding Rae1 β- or H60-transduced tumor cells. Thus, the ligand-expressing tumor cells successfully vaccinated the mice against ligand-negative tumor cells.

Primary rejection of ligand-transduced EL4 and B16-BL6 cells by naïve mice was mediated by NK cells, but it was not expected that NK cells could provide a "memory" immune response. Indeed, mice pretreated with anti-CD8 antibody before the initial exposure to ligand-transduced tumor cells were unable to reject ligand-negative tumor cells upon rechallenge, despite the fact that the ligand-transduced tumor cells had been rejected in each case. Pretreatment of mice with control Ig did not alter the memory response to ligand negative tumor cells. Thus, although CD8+ T cells were not required to reject the primary inoculum of ligand-transduced EL4 and B16-BL6 cells, they were essential for a protective immune response against untransduced tumor cells.

Our results demonstrate that NKG2D ligand expression and consequent activation of NK cells and/or T cells can impose a substantial barrier to the establishment of tumors in vivo. NKG2D associates in the membrane with KAP/DAP10, an adapter signaling protein that is thought to deliver costimulatory signals[12,20]. It is unknown whether NKG2D engagement in NK cells results in direct stimulation or supplies a costimulatory signal that acts in conjunction with signals from other stimulatory receptors[21,22]. Regardless, NKG2D receptor engagement clearly dramatically enhances the effective NK cell response against the tumor cell lines studied here. Our data indicate that ligand expression by tumor cells also directly stimulates (or costimulates) NKG2D-expressing anti-tumor CD8 T cells, in line with recent evidence that cells expressing the human NKG2D ligand, MICA, costimulate responses by antigen-specific human CD8+ T cells[23]. Consistent with this idea, $10^5$ ligand-expressing RMA cells, but not the same number of ligand-negative RMA cells, induced primary rejection of tumor cells by CD8 T cells in the absence of NK cells. Furthermore, all ligand-expressing tumor cells induced CD8 cell-dependent immunity to corresponding ligand-negative tumor cells.

The effectiveness of ligand transduction of tumor cells in stimulating an anti-tumor response and protective immunity to tumor rechallenge indicates that ligand-expressing cells have applications in tumor therapy and the development of tumor vaccines. The strong response against B 16-BL6 cells is particularly notable in this regard, given that the BL6 variant was selected for high invasiveness and is poorly immunogenic[24]. Indeed, other manipulations such as ectopic B7 expression or CTLA4-blockade do not, by themselves, result in rejection of B16-BL6 cells[23]. By providing for enhanced levels of an NKG2D ligand, particularly relative to the density on the host tumor cells, we can effectively boost the anti-tumor immune response and confer or enhance at least partial protective immunity and reduce remission.

Methods. Ectopic expression of NKG2D ligands. Three NKG2D ligand negative cell lines (EL4, a B6 thymoma; RMA, a B6 T lymphoma derived from the Rauscher virus-induced RBL-5 cell line[2] and B16-BL6, a B6 melanoma derived from the B16-F0 cell line[24]) were retrovirally transduced as described[14]. The retroviral vectors containing the H60 or Rae1 β cDNAs used for these experiments did not direct synthesis of GFP or any other selection marker. Transduced cells expressing equivalent high levels of the NKG2D ligands were sorted after staining with a tetrameric soluble version of NKG2D[14]. Control staining was performed with an irrelevant tetramer of the T22 class Ib molecule. Control tumor cells were infected with "empty" retrovirus, and transduced clones were identified by PCR with primers corresponding to the MSCV 5' and 3' LTR. Approximately 100–150 clones with integrated provirus were pooled and used as control tumor cells.

Mice, antibody depletion, tumor inoculation and rechallenge. C57BL/6J (B6) and B6-Rag1$^{-/-}$ mice were purchased from Jackson Laboratories and the latter mice were bred in our animal facilities under specific pathogen free conditions. All mice were used between 8 and 18 weeks of age. NK cells and CD8+ T cells were depleted by injection of 200 μg of monoclonal antibody (PK136 against NK1.1[26] and 2.43 against CD8[27]) at day −1, 1, 8, and 15. Control mice received the equivalent amounts of mouse IgG. Depletions were confirmed in lymph node and spleen cells 3 weeks after tumor challenge by flow cytometry using non-competing antibodies. In general, less than 1.5% of the depleted cell population could be detected in spleen and lymph nodes. Tumor cells were injected subcutaneously in 100 μl of PBS in the right flank. Tumor development was monitored by measuring the tumor size twice weekly with a metric caliper[28]. For the metastasis assay, $3\times10^5$ B16-BL6 cells were injected intravenously via the tail vein, and lung metastases were examined 14–21 days later. For the rechallenge experiments, mice that had completely rejected the initial tumor (8–12 weeks after initial tumor challenge) were injected in the opposite flank with the respective control transduced tumor cells (i.e., lacking NKG2D ligands).

Ex vivo analysis of NK cell activation. Tumor cells were irradiated (10,000 rad) and injected intraperitoneally as described[19]. After 72 h peritoneal cells were harvested[19], and NK cell cytotoxicity was assayed in a standard 4 h $^{51}$Cr release assay[14] or by restimulating NK cells with YAC-1 target cells and staining intracellular IFN-g as described[29]. The number of NK cells in the peritoneal cavity was quantified by flow cytometry and electronic gating on lymphocytes ($FSC^{lo}/SSC^{lo}$). In some experiments NK1.1$^+$ cells were depleted prior to the cytotoxicity assay by complement-mediated lysis as described[30].

Numerically cited references:

1. Trinchieri, G. Biology of natural killer cells. Adv. Immunol. 47, 187–376 (1989).
2. Karre, K., Ljunggren, H. G., Piontek, G. & Kiessling, R. Selective rejection of H-2-deficient lymphoma variants suggests alternative immune defense strategy. Nature 319, 675–678 (1986).
3. Seaman, W., Sleisenger, M., Eriksson, E. & Koo, G. Depletion of natural killer cells in mice by monoclonal antibody to NK-1.1. Reduction in host defense against malignancy without loss of cellular or humoral immunity. J. Immunol. 138, 4539–4544 (1987).
4. van den Broek, M., et al. Decreased tumor surveillance in perforin-deficient mice. J. Exp. Med. 184, 1781–1790 (1996).
5. Kaplan, D. H., et al. Demonstration of an interferon gamma-dependent tumor surveillance system in immunocompetent mice. Proc. Natl. Acad. Sci. USA 95, 7556–61 (1998).
6. Smyth, M. J., et al. Perforin-mediated cytotoxicity is critical for surveillance of spontaneous lymphoma. J. Exp. Med. 192, 755–760 (2000).
7. Kim, S., Iizuka, K., Aguila, H. L., Weissman, I. L. & Yokoyama, W. M. In vivo natural killer cell activities revealed by natural killer cell-deficient mice. Proc. Natl. Acad. Sci. USA 97, 2731–2736 (2000).
8. Smyth, M., Godfrey, D. & Trapani, J. A fresh look at tumor immunosurveillance and immunotherapy. Nature Immunology 2, 293–9 (2001).
9. Houchins, J. P., Yabe, T., McSherry, C. & Bach, F. H. DNA sequence analysis of NKG2, a family of related cDNA clones encoding type II integral membrane proteins on human natural killer cells. J. Exp. Med. 173, 1017–20 (1991).
10. Vance, R. E., Tanamachi, D. M., Hanke, T. & Raulet, D. H. Cloning of a mouse homolog of CD94 extends the family of C-type lectins on murine natural killer cells. Eur. J. Immunol. 27, 3236–3241 (1997).
11. Ho, E. L., et al. Murine Nkg2d and Cd94 are clustered within the natural killer complex and are expressed independently in natural killer cells. Proc. Natl. Acad. Sci. USA 95, 6320–6325 (1998).
12. Wu, J., et al. An activating immunoreceptor complex formed by NKG2D and DAP10. Science 285, 730–2 (1999).
13. Bauer, S., et al. Activation of NK cells and T cells by NKG2D, a receptor for stress-inducible MICA. Science 285, 727–9 (1999).
14. Diefenbach, A., Jamieson, A. M., Liu, S. D., Shastri, N. & Raulet, D. H. Ligands for the murine NKG2D receptor: expression by tumor cells and activation of NK cells and macrophages. Nature Immunology 1, 119–126 (2000).
15. Cerwenka, A., et al. Retinoic acid early inducible genes define a ligand family for the activating NKG2D receptor in mice. Immunity 12, 721–727 (2000).
16. Cosman, D., et al. ULBPs, novel MHC class I-related molecules, bind to CMV glycoprotein UL16 and stimulate NK cytotoxicity through the NKG2D receptor. Immunity 14, 123–133 (2001).
17. Nomura, M., et al. Genomic structures and characterization of Rae1 family members encoding GPI-anchored cell surface proteins and expressed predominantly in embryonic mouse brain. Journal of Biochemistry 120, 987–95 (1996).
18. Groh, V., et al. Broad tumor-associated expression and recognition by tumor-derived gamma delta T cells of MICA and MICB. Proc. Natl. Acad. Sci. USA 96, 6879–84 (1999).
19. Glas, R., et al. Recruitment and activation of natural killer (NK) cells in vivo determined by the target cell phenotype: An adaptive component of NK cell-mediated responses. J. Exp. Med. 191, 129–138 (2000).
20. Chang, C., et al. KAP10, a Novel Transmembrane Adapter Protein Genetically Linked to DAP12 but with Unique Signaling Properties. J. Immunol. 163, 4652–4654 (1999).
21. Pende, D., et al. Identification and molecular characterization of NKp30, a novel triggering receptor involved in natural cytotoxicity mediated by human natural killer cells. J. Exp. Med. 190, 1505–16 (1999).
22. Moretta, L., et al. Activating receptors and coreceptors involved in human natural killer cell-mediated cytolysis. Annu. Rev. Immunol. 19, 197–223 (2001).
23. Groh, V., et al. Costimulation of CD8 ab T cells by NKG2D via engagement by MIC induced on virus-infected cells. Nature Immunology 2, 255–260 (2001).
24. Hart, I. R. The selection and characterization of an invasive variant of the B16 melanoma. American Journal of Pathology 97, 587–600 (1979).
25. van Elsas, A., Hurwitz, A. A. & Allison, J. P. Combination immunotherapy of B16 melanoma using anticytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J. Exp. Med. 190, 355–366 (1999).
26. Koo, G. C. & Peppard, J. R. Establishment of monoclonal anti-NK-1.1 antibody. Hybridoma 3, 301–303 (1984).
27. Sarmiento, M., Glasebrook, A. L. & Fitch, F. W. IgG or IgM monoclonal antibodies reactive with different determinants on the molecular complex bearing Lyt 2 antigen block T cell mediated cytolysis in the absence of complement. J. Immunol. 125, 2665 (1980).
28. Hanson, H. L., et al. Eradication of established tumors by CD8+ T cell adoptive immunotherapy. Immunity 13, 265–76 (2000).

29. Murali-Krishna, K., et al. Counting antigen-specific CD8 T cells: a reevaluation of bystander activation during viral infection. Immunity 8, 177–187 (1998).

30. Liao, N., Bix, M., Zijlstra, M., Jaenisch, R. & Raulet, D. MHC class I deficiency: susceptibility to natural killer (NK) cells and impaired NK activity. Science 253, 199–202 (1991).

II. Ligand expressing tumor cells induce a therapeutic immune response to ligand-negative tumor cells injected contemporaneously at a different site.

Mice were inoculated subcutaneously on one flank with control-transduced tumor cells (i.e. NKG2D-ligand negative) that is normally lethal. On the other flank, the mice were inoculated with buffer (PBS) as a control, or with the same type of tumor cells that had been transduced with the ligand indicated. Time delays between the first and second inoculations are set at zero (contemporaneous inoculations), three days and ten days. For the B16-BL6 model, the dosage used was $5\times10^3$ tumor cells on each side; for the RMA model, the dosage used was $5\times10^4$ tumor cells on each side.

If none of the treatment groups do PBS or control cells protect the mice; however the transduced tumor cells result in complete or nearly complete protection in all treatment groups. For example, the zero delay B16-BL6 group presented 100% mortality in the control group by 30 days and 0% mortality in the treatment group. Our data demonstrate that the transduced tumor cells induce a response that results in rejection of the ligand-negative tumor cells.

III. Ligand expressing tumor cells induce a therapeutic immune response to prostate tumor metastases.

In the present study, we adapted experimental protocols of Kwon et al. (Proc. Natl. Acad. Sci. USA Vol. 96, Issue 26, 15074–15079, 1999) to demonstrate that NKG2D-ligand transduced cells can be used as an adjunctive form of immunotherapy to eliminate residual prostate cancer metastases after primary tumor removal. For these studies, an immunocompetent model that nominally recapitulates clinical metastatic cancer relapse after complete primary tumor resection is used. The establishment of this model is significant because, in general, the development of adjunctive cancer therapies has been markedly hindered by the absence of animal models that mimic metastatic disease relapse after complete primary tumor removal. The TRAMP-derived murine prostate cancer cell line, TRAMP-C2 (C2), is not only tumorigenic, but also metastasizes to regional lymph nodes, submandibular salivary gland and lungs after a chronic interval of primary tumor growth. C2 primary tumors can be completely resected with a very low frequency of local recurrence. After primary tumor removal, nearly all mice experience metastatic relapse arising from established micrometastases that are present at the time of primary tumor resection. The primary site of metastatic C2 relapse in this model is the regional draining lymph nodes in close proximity to the primary tumor. Using this model, we demonstrate that NKG2D-ligand transduced cells, when administered as an adjunctive form of immunotherapy, can reduce the incidence of metastatic relapse by causing the elimination of established micrometastases already present at the time of surgery.

Growth and Maintenance of Cell Lines. The C2 cell line is an early passage line derived from the TRAMP mouse that spontaneously develops autochthonous tumors attributable to prostate-restricted SV(40) T antigen (Tag) expression. Consistent with its prostate epithelial origin, C2 expresses androgen receptor, E-cadherin, and cytokeratin. Roughly one-third of in vivo C2 tumors also express probasin, a secretory protein that is specifically elaborated by the luminal epithelial cells of the rodent prostate. C2 cells are cultured and maintained as described in Kwon et al., Proc. Natl. Acad. Sci. USA Vol. 94, 8099–8103, 1997. Before injection of C2 into syngeneic male C57BL/6 mice, cell suspensions are washed three times in serum-free DMEM. Mice are injected with $2.5–5\times10^6$ cells in 0.1 ml of serum-free DMEM. Injections are delivered subcutaneously between the scapulae by using a 19-gauge needle.

Retroviral Constructs and Transduction. Constructs, transductions and cells are produced as described in Cosman et al., Immunity 14, 123–133. Briefly, cells are transduced with amphotropic retroviruses generated using the LZRSpBMN-Z vector (Kinsella and Nolan, Hum. Gene Ther. 7, 1405–1423, 1996) in the Phoenix packaging line. Transduced cells expressing class I, MICA, and the ULBP antigens are selected using magnetic beads. Transduced cells are stained with monoclonal antibodies specific for the antigens of interest followed by PE-conjugated sheep anti-mouse IgG. Stained cells are incubated with anti-PE microbeads and passed over MACS separation columns according to manufacturer's specifications (Miltenyi Biotec). To isolate cell populations expressing homogeneous levels of the antigen of interest, these cells are further sorted by flow cytometry.

Animal Surgery and Tumor Kinetic Studies. Animal experiments are conducted in accordance with National Institutes of Health Animal Care and Use Guidelines. Six- to eight-week old male C57BL/6 mice are obtained from The Jackson Laboratory. When tumor base area achieves 250 $mm^2$, 6 weeks after C2 cell injection, mice are anesthetized and tumors resected. In Experiment 1, C2 tumors are removed by sharply incising the skin immediately adjacent to the tumor base and then shelling the tumor out from its investing tissues. To further diminish local tumor recurrence (experiments 2 and 3) the surgical procedure is modified by widening the resection margin around the tumor to 0.5 cm. Additionally, the anterior limit of tumor resection is extended to the fascia of the back musculature, and the lateral margins extended to, but does not include, the axillary lymph nodes. All investing tissues are removed en bloc with the tumor left undisturbed within these tissues. After tumor resection, the skin is closed with stainless steel clips. Mice are then randomized into treatment cohorts. During randomization, special care is taken to ensure that cohorts are represented by a similar number of equal-sized tumors resected. Treatment cohorts receive intraperitoneal injections (100 μg) of either NKG2D-ligand transduced cells or sham transduced cells, on days 4, 7, and 10 after surgery. Tumor recurrences at the primary site and within regional and juxta regional lymph nodes are quantified using vernier calipers by obtaining bisecting measurements of recurrent lesions (recorded as square millimeters). Incidences of tumor relapse for control and treated cohorts are compared for statistically significant differences ($P<0.05$) by Student's t test analysis (GRAPHPAD INSTAT 3.00, GraphPad, San Diego).

Histopathologic Analysis of Tissues. Immediately after the killing of mice, recurrent primary tumors, axillary and anterior cervical lymph nodes, salivary glands, and lungs are harvested for histologic examination. These tissues are fixed overnight in zinc-buffered formalin and paraffin-embedded. In some studies, tissues are snap-frozen in OCT compound to permit immunohistologic analysis. Paraffin-embedded tissue sections are stained with hematoxylin and eosin (H&E). To aid in the detection of micrometastases, frozen lymph nodes are immunohistologically stained for cytokeratin by using pan cytokeratin antibody (clone Z0622, Dako) at a 1:1,000 dilution.

NKG2D-ligand Transduced Cells Slow C2 Growth or Cause Its Rejection In C57BL/6 Male Mice. Initial experiments show that in vivo administration of NKG2D-ligand transduced cells can slow the growth, or elicit the rejection, of TRAMP-C1 subcutaneous tumors by the syngeneic non-transgenic C57BL/6 host. In the present study, we further show that in vivo administered NKG2D-ligand transduced cells can elicit a similar response against C2. Like TRAMP-C1, C2 is an early passage prostate cancer cell line that was originally derived from the TRAMP mouse. In separate experiments, mice injected with $2.5\times10^6$ C2 cells are rendered tumor-free for 100 days after treatment with NKG2D-ligand transduced cells. In contrast, mice injected with control cells (sham transduced cells) experience progressive C2 tumor outgrowth. Thus, in vivo administration of NKG2D-ligand transduced cells can raise an antitumoral response sufficient to eradicate C2 after tumor cell challenge.

C2 Primary Tumor Outgrowth Is Accompanied by the Establishment of Regional Lymph Nodes Metastases. In light of the capability of NKG2D-ligand transduced cells to elicit a response against prostate tumors in the subcutaneous murine model, we decided to determine whether NKG2D-ligand transduced cells might be an effective adjunctive treatment to eradicate metastases left in situ after primary tumor removal. To test this, and given that a primary route of prostate cancer dissemination in humans is via lymphatic spread, we use a recently developed model that mimics the proclivity of prostate cancer to metastasize to regional lymph nodes (Kwon et al., Proc. Natl. Acad. Sci. USA Vol. 96, Issue 26, 15074–15079, 1999).

Adjunctive NKG2D-ligand transduced cells Immunotherapy Reduces Metastatic Failure After Primary Tumor Resection. To confirm that adjunctive NKG2D-ligand transduced cells can be used to prevent or reduce treatment failure caused by outgrowth of residual established metastases after surgery, the following studies are performed. Groups of C57BL/6 mice are subject to resection of their dorsal-neck primary C2 tumors when tumor size achieves 250 $mm^2$. On days 4, 7, and 10 after tumor resection, mice are randomized to receive intraperitoneal injections of either the transduced or control cells. After surgery, mice are followed for overt local and/or metastatic C2 outgrowth. Follow-up of mice is begun 21 days after surgery. Mice are killed when the aggregate size of recurrent tumor (primary tumor plus metastatic tumor size) achieves or exceeds 250 $mm^2$. Incidences and distribution of C2 recurrences in individual experiments for both control and NKG2D-ligand transduced cells-treated mice are presented in Table 1.

TABLE 1

Incidences and sites of C2 metastasis/recurrence after treatment. Data reflect percentage of mice with metastases reported according to site of failure.

| Treatment | Regional lymph nodes | Resection site | Lung and/or salivary gland |
|---|---|---|---|
| Control expt 1 | 100 | 70 | 55 |
| Control expt 1 | 100 | 30 | 70 |
| Control expt 1 | 100 | 20 | 60 |
| Treatment expt 1 | 33 | 12 | 15 |
| Treatment expt 1 | 30 | 5 | 19 |
| Treatment expt 1 | 35 | 0 | 12 |

For the three experiments overall, all control-treated mice suffer overt metastatic C2 progression, typically within 40 days after primary tumor removal. Metastatic C2 outgrowth is observed at axillary and/or anterior cervical lymph node sites in all control-treated mice that failed with results approximating those reported in Kwon et al. (supra). In contrast, mice treated with adjunctive NKG2D-ligand transduced cells experience significantly fewer treatment failures.

Adjunctive NKG2D-ligand transduced cells Reduces Surgical Failure by Causing the Elimination of Established C2 Metastases. To further test whether adjunctive NKG2D-ligand transduced cells decrease metastatic failure by causing the elimination of residual C2 metastases after surgery, the following experiment is performed. Mouse cohorts are subject to primary C2 tumor resection and treatment with either NKG2D-ligand transduced cells or control cells. A cohort of non-tumor-bearing mice is sham-operated and included as an additional control group for this study. At 2 weeks after the last day of treatment, axillary and anterior cervical lymph nodes from mice in these cohorts are stained for cytokeratin-positive C2 metastases. Lymph nodes recovered from sham-operated control mice demonstrate extremely weak and nonspecific cytokeratin staining of stromal elements whereas all control tumor-resected mice harbor obvious, intensely cytokeratin-positive, C2 metastases that frequently result in total replacement of normal lymph node architecture. In contrast, most NKG2D-ligand transduced cells-treated mice harbor lymph nodes containing only scattered pyknotic cytokeratin-positive cells or no cytokeratin-positive cells. Hence, adjunctive NKG2D-ligand transduced cells reduce surgical treatment failure by causing the elimination of established C2 metastases left in situ after primary tumor resection.

IV. Ligand expressing tumor cells induce a therapeutic immune response to primary prostate tumors.

In the current study, we adapted the experimental protocols of Hurwitz et al. (Cancer Res. 2000 May 1;60(9):2444–8) to examine the potential of NKG2D-ligand transduced cells in the treatment of primary cancer in TRAMP mice. We find that NKG2D-ligand transduced cells are effective at reducing tumor incidence and the severity of prostatic lesions.

Mice. All animal procedures are performed according to NIH guidelines under protocols approved by the University of California Animal Care and Use Committee. TRAMP mice are bred on a pure C57BL/6 background. In TRAMP mice, the SV40 T antigen transgene expression is under the transcriptional control of the rat probasin promoter that directs expression to prostatic epithelium in an androgen-regulated manner. Pathogenesis of neoplasia in TRAMP mice mirrors that in man. When transgene expression begins at puberty, male TRAMP mice develop hyperplasia (5–8 weeks of age), frank neoplasia (8–12 weeks of age), and eventually invasive adenocarcinoma with metastasis to the lungs, lymph nodes, and bone (15–20 weeks of age). For these experiments, TRAMP mice are backcrossed one time with FVB/N mice and screened for the presence of the transgene by PCR.

Mice receive s.c. vaccinations of $1\times10^6$ NKG2D-ligand transduced TRAMP-C1 or TRAMP-C2 cells, or their untransduced counterparts. Mice are euthanized at the indicated age, and the prostatic complex microdissected under a stereomicroscope. Tumor incidence is initially assessed at necropsy and confirmed by histopathological examination, using a score of 4.0 (see below, invasive adenocarcinoma) as the defining criterion.

Histopathological Analyses. The prostatic complex is microdissected into the individual lobes and fixed in 10% neutral buffered formalin. Tissues are processed and stained with H&E for routine histopathological analyses. TRAMP tissues are graded blindly by two individuals using the following criteria: (a) normal epithelium is assigned a score of 1.0; (b) early signs of prostatic intraepithelial neoplasia with tufting of the epithelium and increased nucleus:cytoplasm ratio are scored as 2.0; (c) more advanced prostatic intraepithelial neoplasia with noted cribiform structures and an increase in mitotic and/or apoptotic figures is scored as 3.0; (d) the loss of interductal spaces and the invasion of basement membranes is scored as 4.0; (e) total loss of ductal lumens with evidence of adenocarcinoma is scored as 5.0; and (f) sheets of anaplastic cells are scored as 6.0. Each arbitrarily numbered sample is scanned for the peak severity at ×4 and graded at a magnification of ×10. To generate a mean peak score, the maximum histological score for the ventral, dorsal, or lateral prostate lobes for each animal is used to calculate a mean for the treatment group. The predominant peak score for all TRAMP animals is 4.0.

Cell Culture. TRAMP-C cells are early passage (10–15 passages in vitro), nonclonal epithelioid tumor cells independently derived from a TRAMP mouse and are propagated as described in Foster et al. (Cancer Res. 57, 3325–2230, 1997). To obtain NKG2D ligand-expressing lines, cells are infected with a retrovirus containing the ligand gene driven by the Maloney murine leukemia virus LTR, using the ψCRIP producer line (Somatix, Inc., Alameda, Calif.), as described (Hurwitz et al., Proc. Natl. Acad. Sci. USA 95, 10067–10071, 1998). Ligand production is assayed by ELISA. Cells used for injection are released from tissue culture dishes with trypsin (BioWhittaker) and washed three times in HBSS (BioWhittaker). Cells are resuspended at a density of $1\times10^7$ cells/ml and injected s.c. in a volume of 0.1 ml.

Reduction of Primary Tumor Incidence in TRAMP Mice following Treatment with Cell-based Vaccines. Given the potency of NKG2D-ligand transduced cells in poorly immunogenic transplantable tumor models (see Example III, herein), we examined the effectiveness of this strategy in the treatment of primary prostatic cancer in TRAMP mice. A cohort of 180 male TRAMP mice receive vaccinations of TRAMP-C1 and TRAMP-C2 (TRAMP-C1/C2) or TRAMP-C1/C2 transduced to express the NKG2D-ligand at about 3.5 months of age. To obtain an early indication of the effectiveness of the treatments, four mice from each group are euthanized 3 weeks after treatment and examined for tumor incidence at gross necropsy and confirmed at the microscopic level. Although no significant differences in mean animal or urogenital tract weight are apparent between the treatment groups, there is a significant difference in tumor incidence. Irrespective of vaccine, all mice receiving control cells have detectable tumor, whereas, only 15% of mice receiving transduced cells have detectable tumor.

At 3 weeks after treatment, the tumors in the control-treated mice are sufficiently large to warrant concern about survival of the remaining mice. Therefore, the remaining 25 mice in each group are euthanized 5 weeks later to allow assessment of tumor incidence and tumor grade. Similar to the analysis at 3 weeks after treatment, there is no significant difference in animal weight or prostate weight between any of the treatment groups. However, a significantly lower tumor incidence is observed in mice treated with the NKG2D ligand-transduced cells.

Reduction of Tumor Grade in TRAMP Mice Treated with NKG2D Ligand-Transduced Cells.

To assess the severity of prostate lesions in TRAMP mice, the individual lobes of the prostate are prepared for routine histopathological analysis and scored as described above. We find a significant reduction in the severity of lesions in mice treated with the transduced cells. Specifically, TRAMP mice treated with ligand-transduced TRAMP-C1/C2 cells have a significantly lower peak score than control-treated mice. In addition, the treatment groups have a significantly lower tumor grade than the control groups. These findings demonstrate that in addition to reducing the incidence of primary tumors, vaccination reduce the severity of prostatic lesions in TRAMP mice. The histological data are also reanalyzed for tumor grade as a function of age at time of treatment. As is the case for tumor incidence, the greatest effect on severity of lesions is found in mice treated at 14 weeks of age.

V. Ligand expressing tumor cells induce a therapeutic response in carcinogen induced tumors.

In the current study, we adapted the experimental protocols of Perletti, et al. (Cancer Res. 2000, 60: 1793–1796) to examine the potential of NKG2D-ligand transduced cells in the treatment of primary cancers induced by chemical carcinogenesis.

Chemical Carcinogenesis. At the age of 50 days virgin Sprague Dawley rats are given 20 mg DMBA dissolved at 45° C. in 1 ml of corn oil through a stomach catheter. Thereafter, rats are examined to monitor the outgrowth of mammary tumors at weekly intervals for the first 3 weeks, and then twice weekly until the first tumor is detected in each rat. Rats showing signs of persistent toxicity due to DMBA administration (diarrhea, fur ruffling, poor mobility) are excluded from the experiment.

Transduction. Palpable tumors are biopsied and isolated tumor cells cultured and transduced with NKG2D-ligand expression vectors essentially as described herein.

Treatment of Rat Mammary Tumors. At the onset of the first palpable tumors, between 40 and 60 days after DMBA administration, rats are allotted to treatment (perfusion of $2\times10^6$ NKG2D-ligand transduced cells) or control (corresponding untransduced cells) groups, alternating between the two. The treatment period is followed by an observation period of 28 days. Tumors are measured weekly with a caliper; tumor volumes are calculated as previously described (O'Reilly et al., Cell 88, 277–285, 1997).

A single intragastric dose of 20 mg of DMBA, administered to immature, virgin rats at 50 days of age, is sufficient to induce the onset within 40–50 days of large, fast-growing tumors, localized in the mammary epithelial area, which have been classified as mammary adenocarcinomas. In carcinogen-fed rats, the onset of the first tumor nodule is detectable by palpation as early as 40 days after DMBA administration, followed by other primary tumors appearing within 7–14 days in the mammary area of the rats, reaching the maximum number of five tumors per animal. At the onset of their first palpable tumor (average volume, 100–200 mm3), rats are randomly divided in two groups: one group of rats is treated with NKG2D-ligand transduced cells, and a second group of control animals is treated with equivalent untransduced cells.

NKG2D-ligand transduced cells show a powerful inhibitory activity on mammary cancer growth. From the second week of treatment (starting at day 7) up to the end of the off-therapy follow-up period, tumor burden values in the treated group are significantly lower than those in controls. At the end of treatment, the ratio between treated tumor volumes and control tumor volumes (T:C ratio) is less than 0.1. Throughout the whole experiment, no sign of toxicity from the transduced cells is detected. During the first week of treatment tumors grow very slowly before they arrest by approximately 8 days.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inhibiting prostate tumor growth in a mammalian host determined to have a metastatic prostate tumor and comprising prostate tumor cells expressing native NKG2D, the method comprising steps:

administering to the mammalian host a host-compatible cell transduced to express on the surface of the cell a plurality of NKG2D-binding moieties of natural NKG2D ligands selected from the group consisting of MICA, MICB and ULBP, wherein the administering step is effective to inhibit growth of the tumor; and detecting a resultant inhibition of growth of the tumor by evaluating growth of the tumor.

2. The method of claim 1, wherein the host-compatible cell is derived from the tumor.

3. A method for inhibiting primary mammary tumor growth in a mammalian host determined to have a primary mammary tumor and comprising mammary tumor cells expressing native NKG2D, the method comprising steps:

administering to the mammalian host a host-compatible cell transduced to express on the surface of the cell a plurality of [A] NKG2D-binding moieties of natural NKG2D ligands selected from the group consisting of MICA, MICB and ULBP, wherein the administering step is effective to inhibit growth of the tumor; and detecting a resultant inhibition of growth of the tumor by evaluating growth of the tumor.

4. The method of claim 3, wherein the host-compatible cell is derived from the tumor.

*5. A method for inhibiting tumor growth in a mammalian host determined to have a tumor arising in situ and comprising tumor cells expressing native NKG2D, the method comprising steps:*

*administering to the mammalian host a composition comprising a multivalent NKG2D-binding agent, wherein the administering step is effective to inhibit growth of the tumor; and*

*detecting a resultant inhibition of growth of the tumor.*

*6. The method of claim 5, wherein the tumor cells express a detectable amount of a native NKG2D ligand.*

*7. The method of claim 5, wherein the tumor cells express a substantially undetectable amount of native NKG2D ligand.*

*8. The method of claim 5, wherein the tumor cells are melanoma cells.*

*9. The method of claim 5, wherein the tumor cells present downregulated MHC class I proteins.*

*10. The method of claim 5, wherein the tumor cells are substantially non-immunogenic in the mammalian host.*

*11. The method of claim 5, wherein the tumor cells are highly metastatic.*

*12. The method of claim 5, wherein the tumor cells are highly tumorigenic.*

*13. The method of claim 5, wherein the administering is remote from the tumor.*

*14. The method of claim 5, wherein the agent comprises a NKG2D-specific antibody.*

*15. The method of claim 5, wherein the agent comprises a NKG2D ligand comprising a plurality of covalently linked natural NKG2D binding moieties.*

*16. The method of claim 5, wherein the agent comprises a NKG2D ligand comprising a plurality of non-covalently linked natural NKG2D binding moieties, wherein the moieties are restricted to a common presenting surface.*

*17. The method of claim 5, wherein the agent comprises a NKG2D ligand comprising a plurality of non-covalently linked natural NKG2D binding moieties, wherein the moieties are restricted to a common presenting surface, wherein the common presenting surface is of a host-compatible cell transformed to express the binding moieties.*

*18. The method of claim 5, wherein the agent comprises a NKG2D ligand comprising a plurality of non-covalently linked natural NKG2D binding moieties, wherein the moieties are restricted to a common presenting surface, wherein the common presenting surface is of a host-compatible cell transformed to express the binding moieties, wherein one or more of the binding moieties are selected from the group consisting of MICA, MICB and ULBP ligand moieties.*

*19. The method of claim 5, wherein the agent comprises a multivalent NKG2D ligand comprising a plurality of non-covalently linked natural NKG2D ligand moieties, wherein the moieties are restricted to a common presenting surface, wherein the common presenting surface is of a host-compatible cell transformed to express the binding moieties, wherein the cell is derived from the tumor.*

*20. The method of claim 5, wherein the agent comprises a multivalent NKG2D ligand comprising a plurality of natural NKG2D ligand moieties, wherein one or more of the moieties are selected from the group consisting of MICA, MICB and ULBP ligand moieties.*

*21. The method of claim 5, wherein the agent comprises a NKG2D ligand comprising a plurality of non-covalently linked natural NKG2D binding moieties, wherein the moieties are restricted to a common presenting surface, wherein the common presenting surface is of a host-compatible cell transformed to express the binding moieties, wherein one or more of the binding moieties are selected from the group consisting of MICA, MICB and ULBP ligand moieties, wherein the cell is derived from the tumor.*

* * * * *